United States Patent [19]

Boehme et al.

[11] 4,132,511
[45] Jan. 2, 1979

[54] DAMPER FOR HIGH PRESSURE PUMPING SYSTEM

[75] Inventors: Detlef R. Boehme, Walnut Creek; Kenneth C. Judah, Napa; Stephen J. Luchetti, Berkeley, all of Calif.

[73] Assignee: Varian Associates, Inc., Palo Alto, Calif.

[21] Appl. No.: 840,710

[22] Filed: Oct. 11, 1977

Related U.S. Application Data

[63] Continuation of Ser. No. 630,102, Nov. 10, 1975, abandoned.

[51] Int. Cl.² ............................................. F04B 11/00
[52] U.S. Cl. ..................................... 417/540; 366/273
[58] Field of Search .................. 417/540, 298; 138/43; 366/273

[56] References Cited

U.S. PATENT DOCUMENTS

| | | | |
|---|---|---|---|
| 2,844,363 | 7/1958 | Clark | 366/273 |
| 2,912,343 | 11/1959 | Collins | 366/273 |
| 2,989,086 | 6/1961 | Dahl | 138/43 |
| 3,245,665 | 4/1966 | Steel | 366/273 |
| 3,276,479 | 10/1966 | Windsor et al. | 138/43 |
| 3,474,831 | 10/1969 | Noakes | 138/43 |
| 3,976,400 | 8/1976 | Major | 417/298 |
| 4,024,061 | 5/1977 | Gatiss | 417/540 |
| 4,054,270 | 10/1977 | Guggor | 366/273 |

Primary Examiner—William L. Freeh
Attorney, Agent, or Firm—Stanley Z. Cole; John J. Morrissey; Gerald M. Fisher

[57] ABSTRACT

A damper for use with a high pressure pumping system, such as a liquid chromatography system, which incorporates a reciprocating pump. The device is a generally enclosed canister including an internally formed flow volume. Inlet and outlet passages through the canister communicate with the flow volume, the inlet passage being connectable to receive the high pressure flow. A compressible body, e.g. of Teflon is positioned in the flow volume. The dimensions of the body are slightly smaller than those of the surrounding volume, whereby the high pressure flow passing between the inlet and outlet flows through the space between the body and the internal canister walls. The compression and decompression of the body in response to the pulsations in the flow dissipate the energy carried by the pulses, thereby damping same.

2 Claims, 2 Drawing Figures

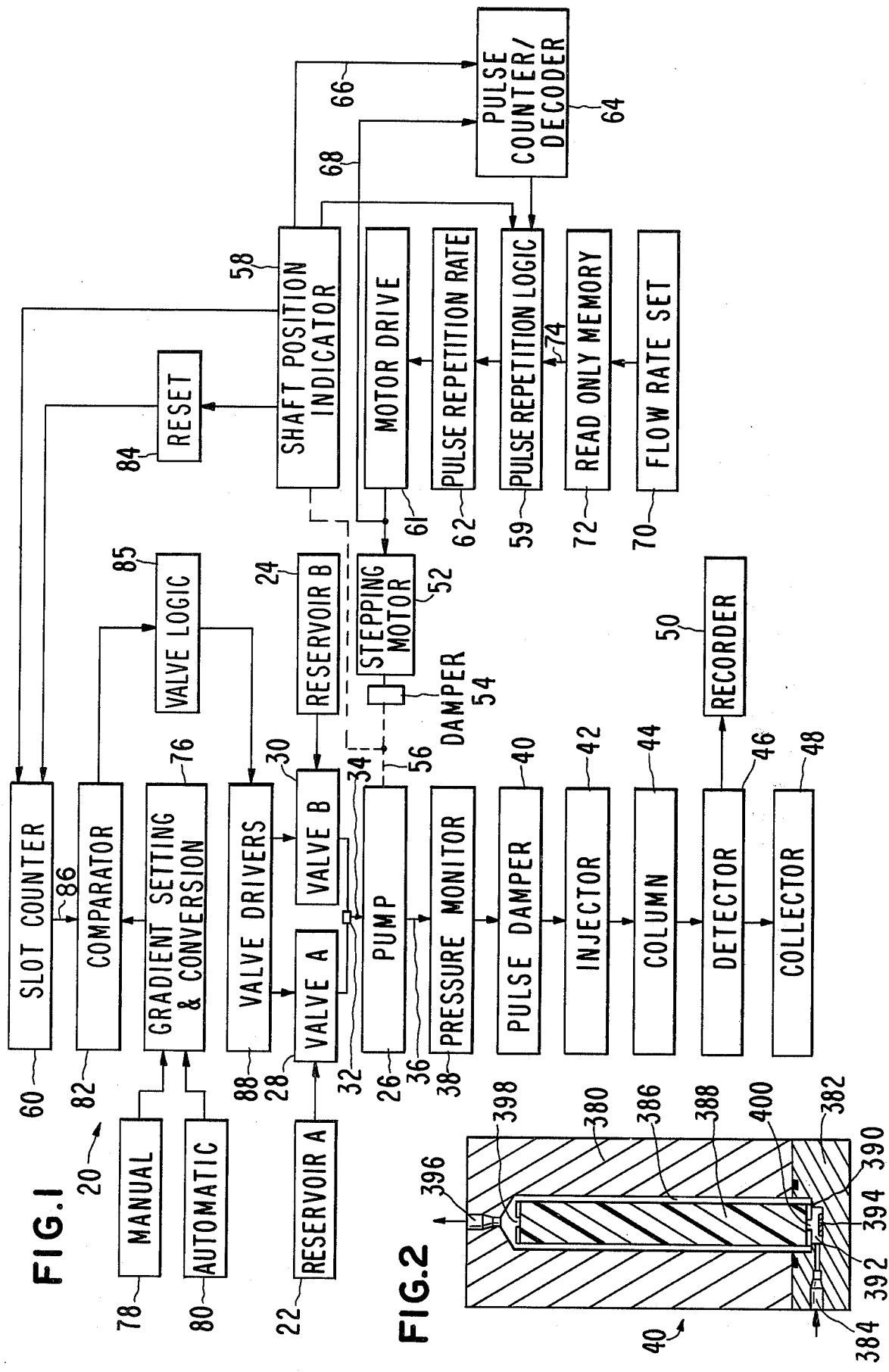

DAMPER FOR HIGH PRESSURE PUMPING SYSTEM

This is a continuation of application Ser. No. 630,102, filed Nov. 10, 1975, now abandoned.

BACKGROUND OF THE INVENTION

This invention relates generally to high pressure pumping systems, and more specifically to a damper for use with a solvent supply system utilized in high performance column liquid chromatography.

Chromatography is a separation method wherein a mixture of components (called the "sample" or "sample mixture") is placed at one end of a system containing a stationary phase and a mobile phase. Each component of the sample distributes itself as a separate zone in dynamic equilibrium between the two phases in a ratio characteristic of that component. As a result, the flowing mobile phase causes each individual component zone to migrate at a characteristic rate, and the zones become separated after a period of time.

There are various types of chromatography, e.g., liquid chromatography, gas chromotography, thin-layer chromatography, etc. The major differences between these various chromatographic methods are the physical state of the mobile phase (gas or liquid), and the manner in which the stationary phase is supported, e.g., whether coated on an inert granular material packed in a tube, coated on an inner wall surface, etc. In each method, the separation mechanism is essentially the same, i.e., distribution of the sample components between a mobile phase and a stationery phase. When the method is used for chemical analysis, a detector is commonly placed at the far end of the system, so as to monitor the passage of the component zones as they emerge from the system. The signal from the detector is displayed on a recording device such as a strip chart recorder, and the record indicates with qualitative and quantitative information regarding the components of the sample.

It is often desirable for a chromatographic system to provide high resolution (i.e., a large degree of component separation with narrow zones), evenly spaced component zones, rapid separation, and a satisfactory record from a very small sample. The behavior of the system described in these terms may be called the "performance" of the system. It is well known in the chromatography art to improve system performance by changing one of the following system variables during the course of the analysis: temperature, chemical composition of the mobile phase, and flow rate of the mobile phase. For example, in gas chromatography the temperature of the system is often varied as a preselected function of time. This technique is known as "temperature programming", and it improves the performance of the system, especially with samples containing components which boil over a wide temperature range. Analagous to temperature programming in gas chromatography is the use of "gradient elution" in liquid chomatography. Gradient elution refers to changing the chemical composition of the mobile phase (also called the "eluent" or "eluting solvent") as a function of time, thereby improving the performance of the system, especially with samples containing components which vary widely in chemical properties. The net effect of gradient elution is to shorten the retention time of compounds strongly retained on columns without sacrifice in separation of early eluting compounds. Further details regarding the fundamentals of gradient elution techniques may be found in numerous sources in the prior art, as, for example, in the publication by L. R. Snyder appearing in *Chromatography Review* 7,1 (1965).

A central concern pertinent to liquid chromatography apparatus of the type considered herein is one of providing a proper flow of solvent to and through the chromatography column. Thus in the past, numerous and varied approaches have been utilized for supplying solvents to high performance liquid chromatography columns. A key requirement in this connection is one of providing a relatively non-pulsating (i.e., a constant) flow of solvent — in that the LC detector is sensitive to flow variations, and can provide erroneous readings and exhibit excessive noise in the presence of pulsing flow. Various approaches have been utilized in the past in order to enable such result; but in general, the prior art methodology directed at such end has involved highly expensive and overly complex mechanisms. Thus, in a typical example wherein a system is intended for operation in a gradient elution mode, i.e., by use of two distinct solvents, a dual pump arrangement may be utilized. Such arrangement requires two distinct pumps, including separate means for driving each of the pumps, which thus requires separate speed controls, etc.

In principle, it would seem that the cited problems arising in connection with the solvent pumping systems of the prior art might be overcome by use of a single cylinder arrangement in cooperation with a relatively small displacement volume reciprocating piston. A principal deterrent to the use of this arrangement, however, has been the fact that the ensuing flow will, by its nature, be pulsating — particularly at low flow rates. Further, the nature of the pulses present in the flow is such that they are not easily removed by filtering, and the presence of such pulses can sharply limit the efficiency of the detector system. It should be understood in the foregoing connection that the word "piston" as used in this specification is intended to include both pistons where the seal remains fixed in relative position to the moving member and plungers where the seal is fixed with respect to the stationary cylinder.

In U.S. Pat. No. 3,985,021 to P. Achener et al. entitled HIGH PERFORMANCE LIQUID CHROMATOGRAPHY SYSTEM, which patent is assigned to the same assignee as the present application, there is disclosed a liquid chromatography system which is particularly useful in overcoming the aforementioned flow problems. The system includes a reservoir for a liquid mobile phase, a liquid chromatography column, reciprocating pumping means for pumping the mobile phase through the column, and motor means for driving the pumping means through successive reciprocation cycles. Means are provided further for controlling the rotational speed of the motor throughout the reciprocation cycle of the pump so as to provide preselected average rotational speeds over predetermined subintervals of each successive reciprocation cycle. Application of the control cycle is synchronized with the pumping cycle so that the speed control is properly applied over each successive reciprocation cycle.

In systems of the cited type, however, as well as in other high pressure liquid pumping systems incorporating reciprocating pumps, pulsation can to varying degrees still occur downstream of the pump thereby prompting interest in damping devices for further reducing or removing same. It has in the past been common to utilize for such purposes dampers which effectively constituted enlarged volumes, e.g. a hollow canister. Such prior art devices, however, introduced an undue amount of volume in the system — which in LC systems interferred with purging and with generation of gradient changes.

In accordance with the foregoing, it may be regarded as an object of the present invention to provide a damper for use with a high pressure pumping system including a reciprocating pump, which damper is of simple, low cost construction, and yet is highly effective in damping pressure pulses.

An additional object of the present invention is to provide a canister type in-line damping device, which while serving very effectively to diminish or remove pulses that may remain following the outlet valve of the system pump nevertheless works with very limited volumes of the flowing liquid, thereby facilitating fast changes in solvent composition, and not impairing purging.

SUMMARY OF INVENTION

Now in accordance with the present invention, the foregoing objects and others as will become apparent in the course of the ensuing specification are achieved in a damper, which while being particularly useful in connection with a liquid chromatography system may also be utilized in other environments where high pressure pumping with reciprocating pumping means introduces pressure pulses that are sought to be filtered or removed. The device is a generally enclosed canister including an internally formed flow volume. Inlet and outlet passages through the canister communicate with the flow volume, the inlet passage being connectable to receive the high pressure flow. A compressible body, e.g., of Teflon or other suitable material having appropriate compressibility and chemical resistance is positioned in the flow volume. The dimensions of the body are slightly smaller than those of the surrounding volume, whereby the high pressure flow passing between the inlet and outlet flows through the space between the body and the internal walls of the canister. The compression and decompression of the body in response to the pulsations in the flow dissipate the energy carried by the pulses, thereby damping same.

In numerous prior art devices dampers have been known for applications such as the present one, but have been based upon highly elaborate devices, or upon constructions which in essence constituted large cavities for the flowing liquids. Such enlarged volumes served to dissipate energy carried by the pulses. These enlarged volumes, however, prevent or restrict fast changes in solvent composition during gradient operation and impair the purging of the system for use with a different solvent.

BRIEF DESCRIPTION OF THE DRAWINGS

The invention is diagrammatically illustrated, by way of example, in the drawings appended hereto, in which:

FIG. 1 is a simplified block diagram setting forth the basic elements of a chromatography system with which the present invention may be utilized; and FIG. 2 is a longitudinal cross-sectional view through a damper in accordance with the invention.

DESCRIPTION OF PREFERRED EMBODIMENT

In FIG. 1 herein, a simplified block diagram appears setting forth the key elements forming part of a liquid chromatography system of a type with which the invention may be utilized. The system 20 corresponds to that disclosed in U.S. Pat. No. 3,985,021 to Achener et al. mentioned above. Reference may be made to that patent for further details of the reciprocating pump, and it will be understood that the discussion herein is intended primarily to illustrate one type of pumping system to which the present invention is, particularly applicable. There is of course, no intention to limit the damper otherwise disclosed to use in this particular high pressyre system.

System 20 is illustrated for use with a pair of reservoirs 22 and 24, each of which contains a distinct solvent, as for example water on the one hand and methanol on the other. The reservoirs are identified for convenience in the Figure as "A" and "B". The solvents are furnished to the pump 26 by means of individual solonoid valves 28 and 30, each of which is associated with a respective one of the reservoirs 22 and 24. These valves, which can be regarded as serving a proportioning function, are identified by designations "A" and "B" — in correspondence to the reservoir identification. The liquids proceeding from valves 28 and 30 enter the mixing Tee 32, which then furnishes the mixed solvent composition via line 34 to the pump 26. The output 36 from the pump may be monitored by a pressure gauge or sensor 38; and safety devices, as for example a rupture disc, may be associated with the continuing in-line flow in order to avoid any possibility of danger arising from excessive pressures — which pressures can be of the order of 5,000 psi or thereabouts. The flow then proceeds through the pulse damper 40 of the details of which will be subsequently set forth. After passing through a conventional injector 42, the flow enters the liquid chromatographic column 44. The output from column 44, as is conventional, may be provided to a detector 46 and thence to a collector 48. Detector 46 may be associated with a suitable recorder 50, again as is known in the art.

Pump 26 is driven by means of a stepping motor 52. Stepping motor 52 is per se conventional. Further a conventional damper 54 may be associated with the stepping motor 52, as for example by being mounted to one end of the drive shaft of the motor. Dampers of this type, suitable for the present purposes, are produced by numerous manufacturers.

The angular rotational velocity of the stepping motor 52 is accurately controlled throughout a 360 degree rotational cycle of its shaft, so as to thereby control the rotational velocity of pump crank shaft 56 which is coupled thereto. Accordingly, shaft position indicator means 58 is provided, which is associated with shaft 56 in a manner as will be subsequently set forth. The shaft position indicator may thus include an encoding wheel provided with peripheral indicia such as slots, which are read by a slot counter 60 during shaft rotation.

The stepping motor 52 is driven by a motor drive 61; which (as is known in the art of driving such motors) provides a series of successive electrical pulses to the stepping motor, which then rotates in steps in accordance with the rate of pulse input. In order to enable the stepping motor to be driven at differing average angular speeds in accordance with its angular position, the shaft position indicator 58 provides a reference signal to pulse repetition logic 59 when the shaft 56 reaches a given point in its angular rotation. In turn, the pulse repetition rate 62 is suitably altered. At the same time, a pulse counter/decoder 64 is enabled through control line 66 and begins to count successive pulses emanating from motor drive 61 via line 68. In the present instance it will thus be noted that the count of drive pulses via line 68 serves as a determinant for the position of the shaft 56 rather than the shaft position indicator directly. This is advantageous in, as will be subsequently seen, some flexibility is present in the shaft and it is considered that less possibility of error can occur by counting the successive pulses than by directly taking the reading from the shaft position indicator. In any event, the counter/decoder 64, having effectively determined the angular position of the shaft, converts the counted pulses to a decoded signal indicating to the pulse repetition rate source 62 the number of pulses per second which are appropriate for the then determined position of shaft 56.

The flow output from pump 26 may vary over a considerable range, as for example from 10 milliliters per hour up to the order of 1,000 milliliters per hour. In order to enable the required variation in pumping speed, a flow rate set means 70 is provided, which may take the form of simple thumb switches. When a given flow rate is set at block 70, a preset programmed read only memory means 72, which has been programmed for the desired flow rate, provides the specified program for each portion of the cycle of operation to the pulse repetition logic 59 via line 74, the pulse repetition logic then controlling the repetition rate accordingly.

In a typical mode of operation of the present system, two solvents may be utilized. The ratio between the two solvents may in some instances be maintained at a relatively constant value; but more commonly the ratio between solvents will vary over the course of a test run, either by manual resetting of the ratio or by automatically controlled programmed changes. A gradient setting and conversion means 76 is thus provided which may either have a manually controlled input setting 78 or may be provided with an automatic gradient program from means 80. Gradient programming, as has been previously indicated, is per se conventional; and accordingly, details of such devices are not set forth herein.

The output from gradient setting and conversion means 76, after conversion to a suitable manipulatable form, is provided to a comparator 82. The numerical count from slot counter 60 is reset once each cycle by reset means 84 upon a reference point being determined during shaft rotation by shaft position indicator 58. When the slot counter 60 output, proceeding via line 86 to comparator 82, equals the converted value provided by gradient setting and conversion means 76, an enabling signal is provided to valve logic 85, which actuates valve drivers 88. These control the opening and closing of valves 28 and 30, which (as has been previously mentioned) operate in substantially complementary fashion — in the sense that when one is open the other is closed. It will thus be evident that by means of the present arrangement one of the valves may be open throughout a portion of the fill cycle for the pump 26 while the other valve is closed; and that throughout the remainder of the fill cycle the reverse is true, i.e., the second valve is open while the first is closed. Thus direct proportioning of the solvent mixture is determined in a very simple manner by deriving control signals in accordance with the angular position of the pump drive shaft, and by utilizing these control signals to divide a subcycle time between feed from the first and second valves in accordance with the gradient setting then appropriate.

By means of the described system, including particularly the unique techniques employed for driving the reciprocating pump 26, a flow is provided at line 36 which is relatively non-pulsating. However, both in system 20 and in other systems of this type, further filtering and damping pulsations is often desired.

In accordance therefore with the invention, such pulsations as may yet remain following the outlet of the reciprocating pump 26 may be further diminished by means of the pulse damper 40 shown in FIG. 2. The device illustrated has several marked advantages in comparison to prior art mechanisms used for this purpose. Basically, the device consists of an upper block 380 and a lower or inlet block 382. The inlet for damper 40 is at 384 and admits liquid as already mentioned, proceeding from the pressure monitor 38, and ultimately from pump 26. An enlarged, generally cylindrically shaped chamber 386 is formed partially in each of the two blocks 380 and 382. These blocks may comprise a metal or other material capable of withstanding the high pressures encountered. An elongated plug 388 of a slightly compressible tough plastic material, preferably Teflon (i.e., polytetrafluoroethylene) or a similar fluorocarbon, is mounted within the extended chamber 386. A shoulder 390 is formed about the bottom of chamber 386 so that a small mixing space 392 is provided beneath the plug. A small magnetic stirrer 394, in the form of a simple bar magnet (as is known in the art) is positioned at the bottom of space 392 and can be actuated by an externally applied rotating magnetic field to ensure that stirring and agitation of the liquid continues during flow. If desired, the mixing stage can also precede the present device instead of being integrated therewith. The outlet 396 from the damper occurs at the top of block 380. The Teflon plug 388 has cross channels at the top and bottom ends thereof, two of which are seen at 398 and 400, with two additional channels running perpendicular to the two indicated. In addition to the cited materials, other materials can be utilized for the compressible body constituting plug 388 — provided that such materials have appropriate compressibility and chemical resistance.

During use, the fluid entering inlet 384 proceeds through the mixing space 392, and thence about the flow space provided between the periphery of plug 388 and the internal walls of pieces 380 and 382. Thence, the said liquid exits through the outlet 396.

Basically, what occurs in the device of FIG. 2 is that pressure pulsations effect compression and subsequent decompression of the Teflon plug, which is thus able to dissipate the energy of such pulses in a very effective manner. In the past, it had been common to utilize dampers which effectively constituted enlarged volumes, e.g., a canister somewhat similar to the present type might be utilized, but without the plug indicated herein. Such prior art devices introduced an undue amount of volume into the system, which interfered with purging and with the generation of gradient changes.

While the present invention has been particularly set forth in terms of specific embodiments thereof, it will be understood in view of the present disclosure that numerous variations upon the invention are now enabled to those skilled in the art, which variations yet reside within the scope of the present invention. Accordingly, the invention is to be broadly construed and limited only by the scope and spirit of the claims now appended hereto.

I claim:

1. In combination with a high pressure liquid pumping system including a reciprocating pump, means for damping pulsations in the liquid flow from said pump, said damping means comprising:

a hollow canister, the interior walls of said canister defining an interior region having a generally elongate dimension;

said canister having inlet means for receiving said liquid flow from said pump into said interior region and outlet means for exit of said liquid flow from said pump out of said interior region, said inlet means being spaced apart from said outlet means along said elongate dimension;

a compressible body positioned in said interior region apart from said inlet means so as to form a mixing volume in said interior region between said inlet means and said compressible body, said compressible body being configured to provide a passageway for said liquid flow from said pump through said canister to said outlet means along a path between said compressible body and the interior walls of said canister, the compression and decompression of said compressible body in response to pulsations in said liquid flow from said pump serving to dissipate the energy carried by said pulses to thereby damp said pulses; and mixing means disposed in said mixing volume for agitating said liquid flow from said pump in said mixing volume.

2. The apparatus of claim 1 wherein said mixing means comprises a bar magnet, whereby agitation of said liquid flow from said pump may be effected by application of a rotating magnetic field in the region of said magnet.

* * * * *